(12) United States Patent
Sommer et al.

(10) Patent No.: US 9,333,341 B2
(45) Date of Patent: May 10, 2016

(54) MEDICAL ELECTRICAL LEAD

(75) Inventors: John Louis Sommer, Coon Rapids, MN (US); Jon D. Schell, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1665 days.

(21) Appl. No.: 12/570,365

(22) Filed: Sep. 30, 2009

(65) Prior Publication Data

US 2011/0077725 A1    Mar. 31, 2011

(51) Int. Cl.
*A61N 1/05* (2006.01)

(52) U.S. Cl.
CPC .............. *A61N 1/056* (2013.01); *A61N 1/0563* (2013.01); *A61N 2001/0585* (2013.01)

(58) Field of Classification Search
USPC ....................................................... 607/36, 37
See application file for complete search history.

(56) References Cited

U.S. PATENT DOCUMENTS

| 3,769,984 | A | 11/1973 | Muench |
| 4,311,153 | A | 1/1982 | Smits |
| 5,003,990 | A | 4/1991 | Osypka |
| 5,304,218 | A | 4/1994 | Alferness |
| 5,381,790 | A | 1/1995 | Kanesaka |
| 5,755,765 | A | 5/1998 | Hyde et al. |
| 5,755,766 | A | 5/1998 | Chastain et al. |
| 5,800,495 | A | 9/1998 | Machek et al. |
| 6,078,840 | A | 6/2000 | Stokes |
| 6,192,280 | B1 | 2/2001 | Sommer et al. |
| 6,901,288 | B2 | 5/2005 | Janke et al. |
| 2006/0074471 | A1* | 4/2006 | Palm .............................. 607/122 |
| 2006/0229693 | A1 | 10/2006 | Bauer et al. |

FOREIGN PATENT DOCUMENTS

EP     0 747 091     12/1996

OTHER PUBLICATIONS

P0035565.01 (PCT/US2010/047950) PCT Notification of Transmittal of the International Search Report and the Written Opinion of the International Searching Authority.

* cited by examiner

*Primary Examiner* — Theodore Stigell
*Assistant Examiner* — Natasha Patel
(74) *Attorney, Agent, or Firm* — Carol F. Barry

(57) ABSTRACT

An implantable lead for placement by means of a guide wire passing therethrough. The lead has an elongated insulative lead body with an axially extending lumen through at least a distal portion of the lead body. A conductor is mounted within and extends to an electrode assembly mounted to a distal portion of the lead body. A seal housing with a seal located therein located at a distal end of the lead body. The seal is located generally perpendicular to the axis of the lead body and is concave on both its proximal and distal sides. The housing is provided with a cavity adjacent each of the seal's proximal and distal sides, into which the seal may be deflected. The electrode assembly may be mounted to the seal housing.

9 Claims, 3 Drawing Sheets

MEDICAL ELECTRICAL LEAD

TECHNICAL FIELD

The invention relates to implantable medical devices and, more particularly, to implantable medical leads.

BACKGROUND

The present invention relates generally to implantable medical leads, and more particularly to implantable leads placed by means of a guide wire.

Most commercially available cardiac pacing and defibrillation leads are placed by means of a stylet which is inserted into a central lumen through the lead, and is used to assist in pushing the lead through the vascular system and guiding it to a desired location. More recently, leads placed by means of a guide wire extending entirely through the lead and out its distal end have been introduced. Although such leads are new to commercial distribution, the basic idea of the guide wire placed lead goes back quite some time. One early example of a guide wire placed pacing lead is disclosed in U.S. Pat. No. 3,769,984 issued to Muench. In this lead, a central lumen extending through the lead and out its distal end is provided which may be used for pressure measurement or for use of a guide wire for guiding the lead during its insertion. In this lead, the guide wire lumen extends along the entire length of the lead body. Similar leads are disclosed in U.S. Pat. No. 5,755,766 issued to Chastain et al, and U.S. Pat. No. 5,800, 495 issued to Machek et al.

In the context of coronary angioplasty catheters, the use of guide wires to place catheters within the vascular system has evolved to include the use of a "monorail" system, in which the guide wire lumen extends over only a distal portion of the catheter body. This basic approach has been adapted to cardiac pacing leads and cardioversion leads as well, as disclosed in U.S. Pat. No. 5,003,990 issued to Osypka, U.S. Pat. No. 5,755,765 issued to Hyde et al, U.S. Pat. No. 5,381,790 issued to Kenasaka and U.S. Pat. No. 5,304,218 issued to Alferness.

In guide wire implanted leads, there is a danger of blood entering the lumen of the lead body through the opening at the distal end of the lead through which the guide wire exits. It has been suggested in the anonymous publication "Guide wire Placement of Electrical Lead" published as publication no. 35442 in Research Disclosure, October 1993, that a pierceable silicone rubber membrane may be located at the distal tip of the lead, to prevent fluid entry into the lead body during and after placement of the lead.

In more recent commercially available leads, a tip seal having a generally cup-shaped configuration has been employed. Representative examples of such leads are illustrated in U.S. Pat. No. 6,192,280, issued to Sommer, et al and US Patent Application Publication No. US2006/0229693 A1 by Bauer, et al., both of which are incorporated herein in their entirety. The seals as disclosed in these references facilitate passage of a guide wire through the seal by allowing for radial expansion of the seal.

An alternative approach is disclosed in U.S. Pat. No. 6,901, 288, issued to Janke, et al., wherein a swellable internal or external seal is provided to seal against fluid entry.

SUMMARY OF THE INVENTION

The present invention is directed to providing an improved tip seal for guide wire placed leads. Unlike the prior art leads discussed above which rely on radial expansion and/or contraction to allow for passage of the guide wire through the seal and provision of a fluid seal thereafter, the present invention provides a seal that employs axial displacement of the seal. The seal's configuration in conjunction with the internal configuration of the housing in which it is mounted provide a seal which allows for repeated movement of a guide wire therethrough in both proximal and distal directions, while still providing a reliable seal after removal of the guide wire.

The invention provides these benefits by means of a generally disc-shaped seal which is concave on both its proximal and distal sides, mounted within a housing which provides a cavity adjacent each of the seal's sides into which the seal may deflect during movement of a guide wire therethrough. The adjacent cavities allow for the center portion of the seal to be displaced axially with the guide wire as it passes through with the guide wire, reducing the drag on the guide wire. This in turn provides for easy passage of the guide wire without increasing the outer diameter of the electrode assembly in which it is mounted and without the complexity of providing a swellable seal as an alternative. The seal design also provides for a wiping action as the guide wire passes through.

The relatively thicker edge portions of the seal allow for a simple but dependable retention mechanism of the seal within a corresponding circumferential groove within the interior of the housing and allow for a simplified assembly process. The seal may be fabricated from a biocompatible elastic material. In the preferred embodiment described herein, the seal is fabricated silicone rubber. The housing in which the seal is located may be fabricated of a biocompatible and more rigid material. In the preferred embodiment described herein, the housing is fabricated of 55D and 75 D polyurethane plastic. Other biocompatible materials may be substituted.

The invention is particularly useful in the context of leads wherein the housing that contains the seal is part of a tip electrode head assembly. In the context of leads for placement in the coronary vasculature, a small diameter at the distal tip, which typically is also a desired location for an electrode, is particularly valuable. The seal and housing design of the present invention also assists in obtaining this result.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF A PREFERRED EMBODIMENT

Figure 1:
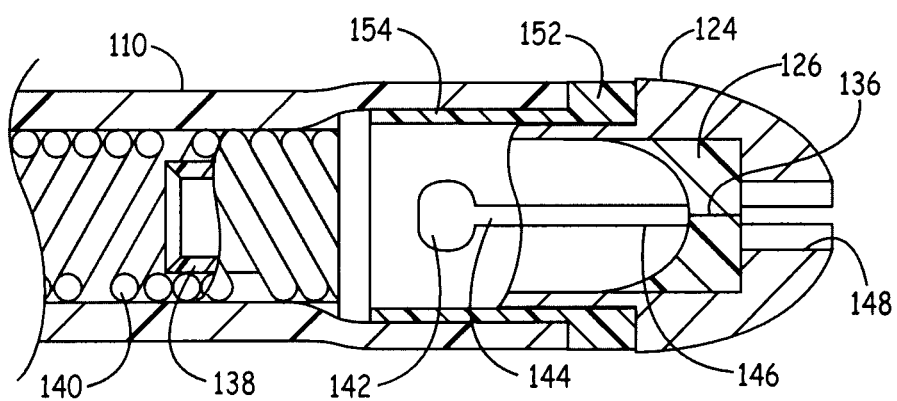
FIG. 1 is a cross sectional view through a prior art lead with an internal tip seal.

FIG. 1 is a sectional view through the distal portion of a lead as described on U.S. Pat. No. 6,192,280, cited above. In this view it can be seen that the electrode 24 is coupled to a coiled conductor 40 by means of an internal crimp sleeve 138. Electrode 124 may be crimped to compress conductor 140 between crimp sleeve 138 and electrode 124. As with the other embodiments described in this prior patent, passage of the guide wire through the seal is facilitated by outward expansion of the seal. A tip seal 126 is located within the electrode 124, rather than extending distally of it. While normally location of a seal within the electrode as illustrated would prevent radial expansion of the seal during passage of the guide wire, electrode 124 is provided with two diametrically opposed longitudinal slots 46, allowing the distal ends of electrode 124 to spread apart from one another due to outward force exerted by seal 126, during passage of a guide wire therethrough. The proximal ends 144 of the slots 146 are optionally provided with enlarged circular recesses 142 to further facilitate the radial opening of the electrode 124. The width of slots 146 is preferably less than the diameter of the guide wire, and is less than the diameter of the distal bore 148, which is slightly larger in diameter than the guide wire to be used with the lead. a preferred material for seal 126 is silicone rubber, and the seal is preferably pre-pierced at 136.

Figure 2:
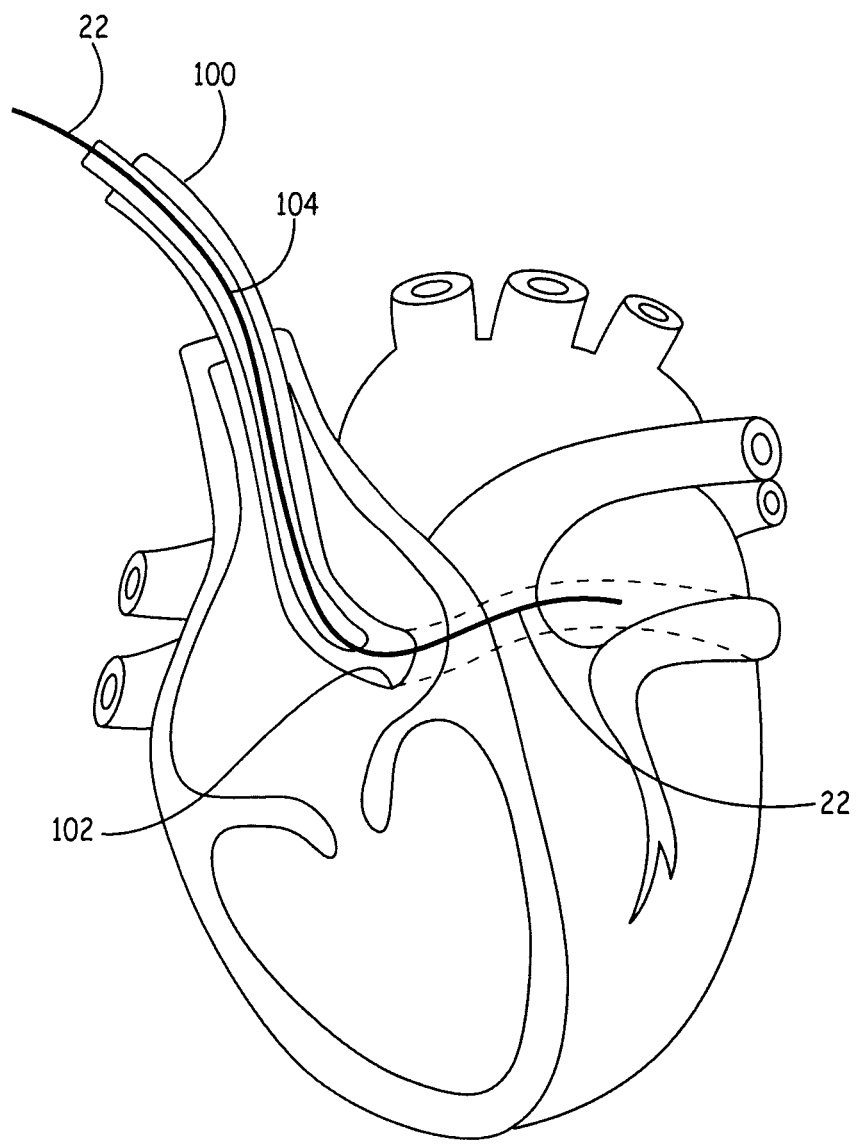
FIG. 2 is a schematic view of a lead of the general type disclosed in the present application as it is inserted into the coronary vasculature.
Figure 3:
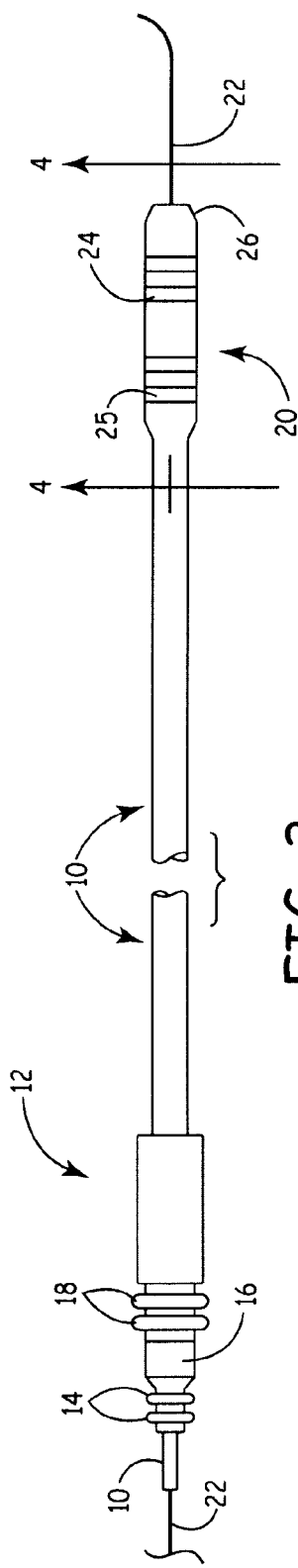
FIG. 3 is a plan view of a preferred embodiment of a lead according to the present invention.
Figure 4:
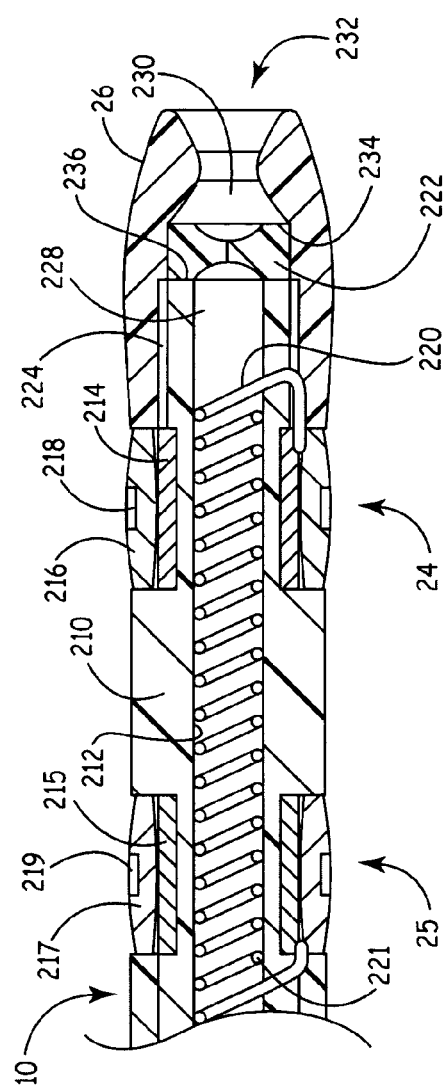
FIG. 4 is a sectional view through the distal portion of the lead of FIG. 3.

FIG. 2 is a schematic diagram of a lead 104 according to the present invention, which may correspond to any of the leads illustrated in FIGS. 3 and 4 or other embodiments of the present invention, passing through a guide catheter 100 and carrying a guide wire 22 extending through the entire length of the lead and out its distal end. As illustrated, the distal end 102 of guide catheter 100 is placed adjacent the opening of the coronary sinus and guide wire 22 extends into the coronary sinus. During implantation of the lead, the tip of guide wire 22 is advanced to a desired location within the patient's vascular system, for example the coronary sinus, and the lead 104 is passed along the guide wire 22 until it reaches its desired location. Use of a guide catheter 100 to facilitate advancement of the guide wire and/or the lead to a position adjacent its desired ultimate location, for example the ostium of the coronary sinus, is optional. After the lead is placed in its desired location, the guide wire 22 and the guide catheter 100 (if provided) are removed.

FIG. 3 illustrates a first embodiment of a lead according to the present invention. The lead is provided with an elongated insulative lead body 10 which in the embodiment illustrated takes the form of single lumen insulative plastic or polymer tube, which carries a coiled conductor therein. Other lead body types may be substituted within the context of the present invention, including lead bodies employing multiple lumen tubes and/or stranded or braided conductors as disclosed in U.S. Pat. No. 5,584,873 issued to Shoberg et al, and incorporated herein by reference in its entirety. Alternatively, the lead may include additional conductors arranged either within a multi-lumen lead body or concentrically, as disclosed in U.S. Pat. No. 4,355,646 issued to Kallok et al and incorporated herein by reference in its entirety. Additional pacing electrodes, sensors, or defibrillation electrodes, may of course be added to the lead body and coupled to additional conductors. In the particular embodiment discussed below, the lead body takes the form of a single lumen elongated tube carrying co-radially wound mutually insulated coiled conductors as described in US Patent Publication No. US 2006/02296933 A1, cited above.

A connector assembly 12 is located at the proximal end of the lead body 10. The connector assembly as illustrated provides a bipolar connector according to the IS-1 industry standard. The connector assembly carries a tubular connector pin 10 and a connector ring 16, each of which are coupled to one of the two mutually insulated conductors within lead body 10. Sealing rings 14 and 18 are provided to seal the connector assembly within the connector bore of an associated cardiac stimulator.

An electrode head assembly is located at the proximal end of the lead body 10. This assembly carries two electrode assemblies 24 and 25. As illustrated the guide wire 22, which may be any appropriate commercially available guide wire or other guide wire according to the prior art is shown entering the connector pin 10, passing through the lumen within the lead body 10 and exiting through the distal tip 26 member of the electrode head assembly. The electrode head assembly is discussed in more detail below in conjunction with FIG. 4.

FIG. 4 is a sectional view through the distal portion of the lead of FIG. 3, illustrating the internal construction of the electrode head assembly 20 (FIG. 1). The electrode head assembly includes a housing comprising a generally cylindrical core 210, with an internal, generally cylindrical lumen 212 in communication with the internal lumen of the lead body 10 and through which the guide wire passes. Core 210 may be fabricated, for example, of 75 D polyurethane plastic. Other biocompatible materials may be substituted. The core, in conjunction with the tip member 26, provide the housing in which the seal 222 is mounted. Tip 26 may be fabricated, for example, of 55D polyurethane plastic. Other biocompatible materials may be substituted. Tip member 26 is attached to core 210 by means of adhesive 224. The tip member 26 is provided with a distal opening 232 through which the guide wire exits the lead distally.

Electrode assemblies 24 and 25 are mounted around the core 210 and correspond to the electrode assemblies disclosed in US Patent Publication No. US 2006/02296933 A1, cited above. The electrode assemblies 24 and 25 include electrode rings 214, 215, monolithic controlled release devices 216, 217 and radio-opaque indicator rings 218 and 219, as described in the cited '933 application. Other electrode configurations, for example simple electrode rings or segmented electrode rings may be substituted.

Electrode rings 214 and 215 are coupled to insulated coiled conductors 220 and 221, which as illustrated correspond to the conductors in the above-cited '933 application. However, other conductor types may be substituted. The co-radial multi-construction as illustrated is particularly useful in conjunction with the present invention as it also assists in reducing the over-all diameter of the electrode head assembly.

The seal 222 as illustrated is generally disc shaped, mounted generally perpendicular to the axis of the lead body 10 as illustrated it has a generally circular circumferential edge which is substantially thicker than it's central region, through which the guide wire passes. Non-circular configurations are also possible. The seal is also preferably pre-pierced in its central portion through which the guide wire is to pass. The piercing may comprise a small, centrally located slit as described and illustrated in the above-cited '280 patent.

The seal is retained within the housing by reason of its location within the internal circumferential groove defined by tip member 26 in conjunction with core 210. Within the housing, cavities 228 and 230 are provided adjacent the proximal and distal surfaces seal 222, open to the lumen of the lead body and to the distal opening of the tip member 26, respectively, into which seal 222 may deflect proximally or distally during passage of a guide wire therethrough.

The seal 222 may easily be mounted within the electrode head assembly by simply placing it in the tip member 26 before mounting it to the distal end of the core 210. As illustrated, the interior of the tip member 26 is provided with a proximally facing circumferential surface 234 which abuts the corresponding distally facing portion of the thickened circumferential edge of the seal 222. Correspondingly, the core 210 is provided with a distally facing circumferential surface 236 which abuts the corresponding proximally facing portion of the thickened circumferential edge of the seal 222. The seal is retained mechanically in the groove defined between these two surfaces.

While the invention as describe above employs the seal and its associated housing as part of the electrode head assembly, it is believed the invention may also be usefully practiced in leads wherein the electrodes are located at a distance from the seal housing. Additionally, while the invention as illustrated takes the form of a lead in which the guide wire passes through the interior of the lead along its entire length, the invention is also believed useful in leads in which the guide wire passes through only part of the length of the lead body, sometimes referred to as "side-wire" or "monorail" configurations. Other modifications to the invention are possible within the scope of the claims which follow.

In conjunction with the above, we claim:

1. An implantable lead, comprising:
   an elongated insulative lead body having an axially extending lumen through at least a distal portion of the lead body;
   an elongated conductor mounted within the lead body and extending along the lead body;
   an electrode assembly mounted to a distal portion of the lead body and coupled to the elongated conductor; and
   a seal housing located at a distal end of the lead body, having a distal opening and a seal located therein, wherein:
   the seal is located generally perpendicular to the axis of the lead body and is generally disc-shaped and is concave on both its proximal and distal sides; and
   the seal housing is provided with a cavity adjacent each of the seal's proximal and distal sides, into which the seal may be deflected, the cavity adjacent the seal's proximal side open to the lead body's lumen and the cavity adjacent the seal's distal side open to the distal opening of the seal housing.

2. A lead according to claim 1, wherein the housing comprises the internal circumferential groove and the seal is retained within the housing by reason of its location within the internal circumferential groove.

3. A lead according to claim 1, wherein the housing is fabricated of a first material and the seal is fabricated of a second material less rigid than the first material.

4. A lead according to claim 1 wherein the seal is pre-pierced.

5. A lead according to claim 1, wherein the seal is provided with a concave surface on one of its proximal and distal sides.

6. A lead according to claim 1, wherein the seal is provided with a concave surface on both its proximal and distal sides.

7. An implantable lead, comprising:
   an elongated insulative lead body having an axially extending lumen through at least a distal portion of the lead body;
   an elongated conductor mounted within the lead body and extending along the lead body;
   an electrode assembly mounted to a distal portion of the lead body and coupled to the elongated conductor; and
   a seal housing located at a distal end of the lead body, having a distal opening and a seal located therein, wherein:
   the seal is located generally perpendicular to the axis of the lead body and is generally disc-shaped and is concave on both its proximal and distal sides; and
   the seal housing is provided with a cavity adjacent each of the seal's proximal and distal sides, into which the seal may be deflected, the cavity adjacent the seal's proximal side open to the lead body's lumen and the cavity adjacent the seal's distal side open to the distal opening of the seal housing; and
   wherein the housing comprises two members, one provided with a proximally facing surface which abuts the distal surface of the seal, the other provided with a distally facing circumferential surface which abuts the proximal surface of the seal and wherein the seal is retained mechanically between these two surfaces.

8. A lead according to claim 7, wherein the proximally and distally facing surfaces of the housing members define a circumferential groove in which the seal is located.

9. An implantable lead, comprising:
   an elongated insulative lead body having an axially extending lumen through at least a distal portion of the lead body;
   an elongated conductor mounted within the lead body and extending along the lead body;
   an electrode assembly mounted to a distal portion of the lead body and coupled to the elongated conductor; and
   a seal housing located at a distal end of the lead body, having a distal opening and a seal located therein, wherein:
   the seal is located generally perpendicular to the axis of the lead body and is generally disc-shaped and is concave on both its proximal and distal sides; and
   the seal housing is provided with a cavity adjacent each of the seal's proximal and distal sides, into which the seal may be deflected, the cavity adjacent the seal's proximal side open to the lead body's lumen and the cavity adjacent the seal's distal side open to the distal opening of the seal housing; and
   wherein the electrode assembly is mounted to the seal housing.

* * * * *